(12) United States Patent
Kleinert et al.

(10) Patent No.: US 10,557,829 B2
(45) Date of Patent: Feb. 11, 2020

(54) TWO-DIMENSIONAL TR PROBE ARRAY

(71) Applicant: General Electric Company, Schenectady, NY (US)

(72) Inventors: Wolf-Dietrich Kleinert, Bonn (DE); Mark Howard Feydo, Reedsville, PA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/159,307

(22) Filed: Oct. 12, 2018

(65) Prior Publication Data

US 2019/0079057 A1    Mar. 14, 2019

Related U.S. Application Data

(63) Continuation of application No. 15/176,401, filed on Jun. 8, 2016, now Pat. No. 10,126,270, which is a
(Continued)

(51) Int. Cl.
*G01N 29/22* (2006.01)
*G01N 29/04* (2006.01)

(52) U.S. Cl.
CPC .......... *G01N 29/043* (2013.01); *G01N 29/22* (2013.01); *G01N 2291/0289* (2013.01); *G01N 2291/044* (2013.01); *G01N 2291/106* (2013.01)

(58) Field of Classification Search
CPC ................. G01N 29/043; G01N 29/22; G01N 2291/0289; G01N 2291/106; G01N 2291/044
(Continued)

(56) References Cited

U.S. PATENT DOCUMENTS 3,816,774 A    6/1974    Ohnuki
4,881,409 A    11/1989    Roarty
(Continued)

FOREIGN PATENT DOCUMENTS

DE           10018355 A1    12/2001
DE       102012201715 A1     9/2012
(Continued)

OTHER PUBLICATIONS

International Search Report and Written Opinion issued in connection with corresponding PCT Application No. PCT/US2013/068638 dated Jun. 4, 2014.

*Primary Examiner* — Jacques M Saint Surin
(74) *Attorney, Agent, or Firm* — Mintz Levin Cohn Ferris Glovsky and Popeo, P.C.

(57) ABSTRACT

An ultrasonic sensor assembly includes a flexible supporting material that has flexibility configured for allowing bending of the supporting material to conform to a cylindrical shape of a pipe. The assembly includes a plurality of operable sensor elements arranged in a matrix formation upon the flexible supporting material. The matrix formation includes a plurality of rows of the sensor elements and a plurality of columns of the sensor elements. The flexible supporting material is configured for placement of the columns of the matrix formation to extend along the elongation of the pipe and the flexible supporting material is configured for placement of the rows of the matrix formation to extend transverse to the elongation of the pipe. The flexible support material is configured to flex for positioning the sensor elements within each row in a respective arc that follows a curve of the cylinder shape of the pipe.

20 Claims, 3 Drawing Sheets

Related U.S. Application Data continuation of application No. 13/680,183, filed on Nov. 19, 2012, now Pat. No. 9,404,896.

(58) Field of Classification Search
USPC .......................................................... 73/628
See application file for complete search history.

(56) References Cited

U.S. PATENT DOCUMENTS

| | | |
|---|---|---|
| 5,174,164 A | 12/1992 | Wilheim |
| 5,851,187 A | 12/1998 | Thomas et al. |
| 6,792,808 B1 | 9/2004 | Batzinger et al. |
| 6,813,950 B2 | 11/2004 | Glascock |
| 7,093,490 B2 | 8/2006 | Kono et al. |
| 7,165,453 B2 | 1/2007 | Flora |
| 7,324,910 B2 | 1/2008 | Struempler et al. |
| 7,698,946 B2 * | 4/2010 | Clarke ................... G03B 29/00 600/437 |
| 7,878,977 B2 | 2/2011 | Mo et al. |
| 8,649,185 B2 | 2/2014 | Wodnicki et al. |
| 8,924,164 B2 | 12/2014 | Baba et al. |
| 9,404,896 B2 | 8/2016 | Kleinert et al. |
| 10,126,270 B2 | 11/2018 | Kleinert et al. |
| 2003/0172735 A1 * | 9/2003 | Lam ................... G01N 29/0609 73/622 |
| 2004/0024320 A1 | 2/2004 | Karasawa et al. |
| 2004/0024420 A1 | 2/2004 | Karasawa et al. |
| 2004/0249285 A1 | 12/2004 | Deng et al. |
| 2005/0068041 A1 * | 3/2005 | Kress ................. G01N 29/2475 324/527 |
| 2005/0081636 A1 | 4/2005 | Barshinger et al. |
| 2007/0150238 A1 | 6/2007 | Struempler et al. |
| 2008/0015443 A1 | 1/2008 | Hosono |
| 2010/0199770 A1 | 8/2010 | Kleinert |
| 2010/0207642 A1 | 8/2010 | Cristini |
| 2014/0000371 A1 | 1/2014 | Engl et al. |
| 2014/0157903 A1 | 6/2014 | Oberdoerfer et al. |
| 2014/0238136 A1 | 8/2014 | Ten Grotenhuis et al. |
| 2015/0041616 A1 * | 2/2015 | Gentile ................ G06Q 10/087 248/550 |
| 2015/0219602 A1 | 8/2015 | Bond-Thorley et al. |

FOREIGN PATENT DOCUMENTS

| | | |
|---|---|---|
| EP | 1348954 A1 | 10/2003 |
| WO | 2008155645 A2 | 12/2008 |
| WO | 2009015940 A2 | 2/2009 |
| WO | 2012056218 A1 | 5/2012 |
| WO | 2014023938 A2 | 2/2014 |

* cited by examiner

TWO-DIMENSIONAL TR PROBE ARRAY

CROSS REFERENCE TO RELATED APPLICATIONS

This application is a continuation of, and claims priority to, U.S. application Ser. No. 15/176,401, entitled "TWO-DIMENSIONAL TR PROBE ARRAY," filed Jun. 8, 2016, which is a continuation of, and claims priority to, U.S. patent application Ser. No. 13/680,183 (now U.S. Pat. No. 9,404,896), entitled "TWO-DIMENSIONAL TR PROBE ARRAY," filed Nov. 19, 2012, which are hereby incorporated by reference in their entireties.

FIELD

The present invention relates generally to ultrasonic sensor assemblies, and more particularly, to an ultrasonic sensor assembly including a sensor array of sensor elements.

BACKGROUND

Ultrasonic sensor assemblies are known and used in many different applications. Ultrasonic sensor assemblies are used, for example, to inspect a test object and detect/identify characteristics of the test object, such as corrosion, voids, inclusions, length, thickness, etc. In pipeline corrosion monitoring applications, the test object typically includes a metallic pipe. In such an example, a transmitter-receiver ("TR") probe is provided for detecting/identifying the characteristics of the pipe. However a single TR probe occupies a relatively small area and, thus, has a relatively small testing range. Also, the pipe may have an arcuate contour surface. Detecting characteristics of the entire pipe with one TR probe can be inaccurate and time consuming. Accordingly, it would be beneficial to provide an ultrasonic sensor assembly that can address such issues. Further, it would be beneficial to provide this sensor array with a contoured shape that matches the shape of the test object.

SUMMARY

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, the present invention provides an ultrasonic sensor assembly for testing a tubular pipe that has a cylindrical shape and has an elongation along the extent of the pipe. The ultrasonic sensor assembly includes a flexible supporting material that has flexibility configured for allowing bending of the supporting material to conform to the cylindrical shape of the pipe. The ultrasonic sensor assembly includes a plurality of operable sensor elements arranged in a matrix formation upon the flexible supporting material. The matrix formation includes a plurality of rows of the sensor elements and a plurality of columns of the sensor elements. The flexible supporting material is configured for placement of the columns of the matrix formation to extend along the elongation of the pipe and the flexible supporting material is configured for placement of the rows of the matrix formation to extend transverse to the elongation of the pipe. The flexible support material is configured to flex for positioning the sensor elements within each row in a respective arc that follows a curve of the cylinder shape of the pipe.

In accordance with another aspect, the present invention provides a method for testing a tubular pipe that has a cylindrical shape and that has an elongation along the extent of the pipe using an ultrasonic sensor assembly. The method includes providing the ultrasonic sensor assembly. The assembly includes a flexible supporting material that has flexibility configured for allowing bending of the supporting material to conform to the cylindrical shape of the pipe. The assembly includes a plurality of operable sensor elements arranged in a matrix formation upon the flexible supporting material. The matrix formation includes a plurality of rows of the sensor elements and a plurality of columns of the sensor elements. The flexible supporting material is configured for placement of the columns of the matrix formation to extend along the elongation of the pipe and the flexible supporting material is configured for placement of the rows of the matrix formation to extend transverse to the elongation of the pipe. The flexible support material is configured to flex for positioning the sensor elements within each row in a respective arc that follows a curve of the cylinder shape of the pipe. The method includes placing the ultrasonic sensor assembly onto the pipe. The step of placing the assembly includes engaging the flexible supporting material to the pipe to place the columns of the matrix formation extending along the elongation of the pipe and the rows of the matrix formation extending transverse to the elongation of the pipe. The step of placing the assembly includes bending the flexible support material for positioning the sensor elements within each row in a respective arc that follows a curve of the cylinder shape of the pipe. The method includes operating the sensor elements.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION

Figure 1:
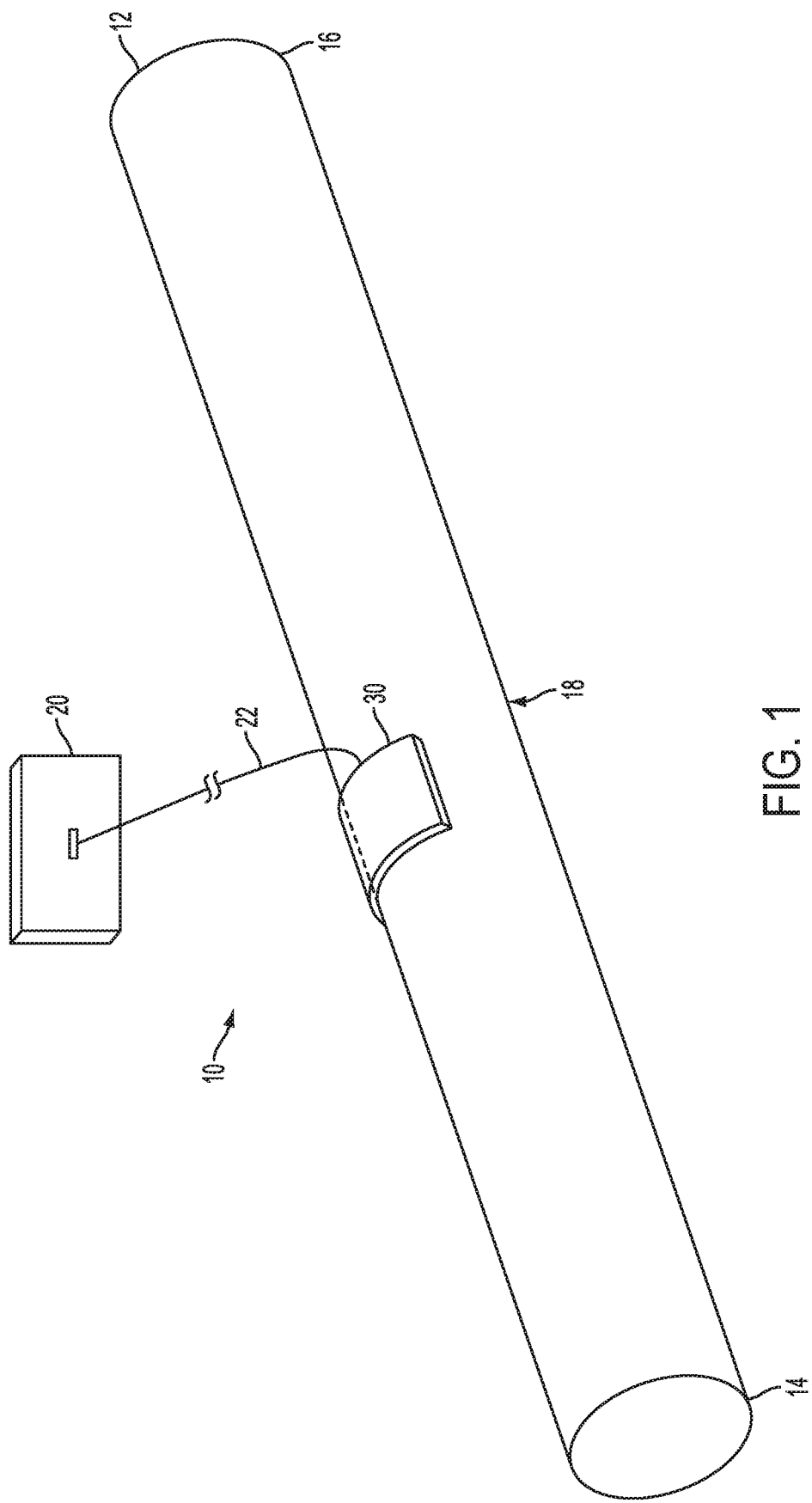
FIG. 1 is a schematic, perspective view of an example ultrasound sensor assembly being used a test object in accordance with an aspect of the present invention.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates a perspective view of an example ultrasonic sensor assembly 10 according to one aspect of the invention. In short summary, the ultrasonic sensor assembly 10 includes a controller 20 and a sensor array 30 that can be positioned in proximity to a test object 12. The sensor array 30 transmits ultrasonic waves into the test object 12 to detect characteristics of the test object 12. These characteristics include corrosion (e.g., thickness and location of corrosion), wall thickness, voids, inclusions, etc. The sensor array 30 is operatively attached to the controller 20 by means of a wire 22 (or may be wireless). To provide improved sensing of the test object 12, the sensor array 30 includes a plurality of sensor elements arranged in a two dimensional array.

The test object 12 is shown to include a tubular pipe having a generally cylindrical shape extending between a first end 14 and an opposing second end 16. The test object 12 can include a non-solid body (e.g., hollow body) or may be solid. It is to be appreciated that the test object 12 is somewhat generically/schematically depicted in FIG. 1 for ease of illustration. Indeed, the test object 12 is not limited to the pipe extending along a linear axis, and may include bends, undulations, curves, or the like. The test object 12 has an outer surface 18 forming a generally cylindrical shape. In other examples, the test object 12 could include other non-cylindrical shapes and sizes. For example, the test object 12 could have a non-circular cross-sectional shape, such as by having a square or rectangular cross-section. In other examples, the test object 12 further includes a tubular shape, conical shape, or the like. Even further, the test object is not limited to pipes, but instead, could include walls, planar or non-planar surfaces, etc. As such, the test object 12 shown in FIG. 1 comprises only one possible example of the test object.

Turning to the controller 20, the controller is somewhat generically/schematically depicted. In general, the controller 20 can include any number of different configurations. In one example, the controller 20 is operatively attached to the sensor array 30 by means of the wire 22. As will be described in more detail below, the controller 20 is configured to send and receive information (e.g., data, control instructions, etc.) from the sensor array 30 through the wire 22. This information can be related to characteristics of the test object 12. For example, in pipeline corrosion monitoring applications, the test object 12 may be susceptible to imperfections, such as corrosion, cracks, voids, inclusions, or the like. As such, this information includes, but is not limited to, dimensions of the test object 12 (e.g., thickness, length, etc.), the presence or absence of corrosion for corrosion mapping, cracks, or the like. The controller 20 can include circuits, processors, running programs, memories, computers, power supplies, ultrasound contents, or the like. In further examples, the controller 20 includes a user interface, display, and/or other devices for allowing a user to control the ultrasonic sensor assembly 10.

Focusing upon the operation of the sensor array 30, the sensor array 30 is placed in proximity to the outer surface 18 of the test object 12 and/or in contact with the outer surface 18. The ultrasonic sensor assembly 10 can include a single sensor array (as shown), or a plurality of sensor arrays. The sensor array 30 is not limited to the position shown in FIG. 1, as the sensor array 30 is moved along the outer surface 18 of the test object 12. Indeed, the sensor array 30 could be positioned at any number of locations along the test object 12, such as closer towards a center, closer towards the first end 14 or second end 16, etc. In one example, the sensor array 30 has a shape that substantially matches a shape of the outer surface 18 of the test object 12. For instance, as shown in FIG. 1, the sensor array 30 includes a curvature that substantially matches a curvature of the test object 12. The curvature could be larger or smaller in further examples, depending on the size and shape of the test object 12. However, in other examples, the sensor array 30 need not have such a curvature, and may instead have a substantially planar shape.

Figure 2:
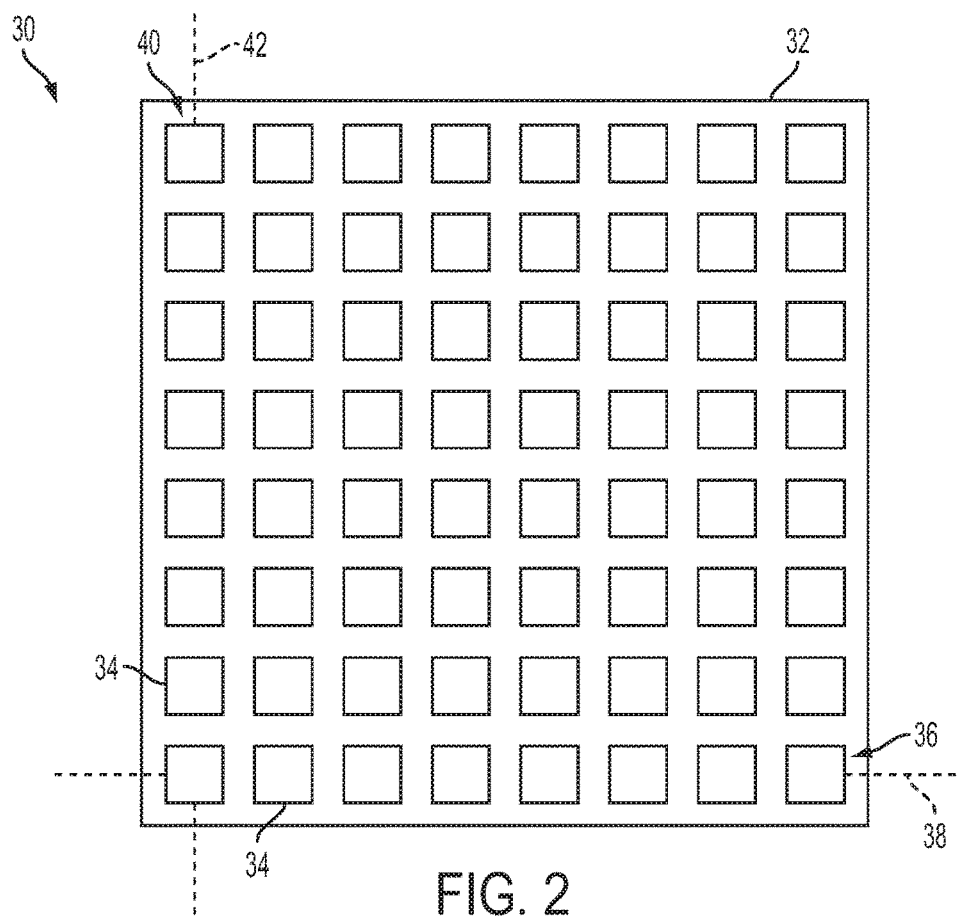
FIG. 2 is a schematic view of an example sensor array of the ultrasound sensor assembly.

Turning now to FIG. 2, the sensor array 30 will be described in more detail. The sensor array 30 is not shown in proximity to the test object 12 in FIG. 2 for illustrative purposes and to more clearly illustrate the elements of the sensor array 30. However, in operation, the sensor array 30 is placed in proximity to the test object 12 as described with respect to FIG. 1.

The sensor array 30 can include a supporting material 32 that provides support to the sensor array 30. In one example, the supporting material 32 is a resilient member having a predetermined shape. The supporting material 32 can be non-flexible or, in other examples, could be provided with some degree of flexibility or movement. As described above, the supporting material 32 can include the curved shape that matches the shape of the outer surface 18 of the test object 12. However, the supporting material 32 could also include the substantially planar shape. The supporting material 32 can include any number of materials, such as engineering plastics, polyimide materials, etc. In further examples, the supporting material 32 could include a flexible or semi-flexible member, allowing for the supporting material 32 to be bent or molded to a desired shape.

The sensor array 30 further includes one or more sensor elements 34 for detecting characteristics of the test object 12. The sensor elements 34 are somewhat generically depicted in FIG. 2, as the sensor elements 34 include a number of different sizes, shapes, and configurations. As shown in FIG. 2, the sensor elements 34 are arranged in a matrix formation. In the matrix formation, the sensor elements 34 may include one or more rows 36 extending along a first direction (e.g. a first axis). Within the shown example of FIG. 2, the first axis 38 extends generally linearly along the sensor array 30. Of course, if the array 30 has a curvature, the first direction can follow along such curvature.

The rows 36 each include a plurality of the sensor elements 34. In the shown example, the rows 36 each include eight sensor elements 34 (as shown) in a sequence, though the rows 36 could include as few as one or more sensor elements or greater than eight sensor elements. The sensor elements 34 within each of the rows 36 are generally equidistant from each other, such that the sensor elements 34 are substantially equally spaced from adjacent sensor elements along the length of the sensor array 30. In further examples, the sensor elements 34 could be spaced closer together or farther apart than as shown. In the shown example, there are eight rows arranged in a non-staggered orientation (i.e., one row above another row), though in further examples, the rows 36 could be staggered with respect to adjacent rows.

The matrix formation of the sensor array 30 further includes one or more columns 40 extending along a second direction (e.g., a second axis). Within the shown example, the second axis 42 extends generally linearly along the sensor array 30 in a direction that is substantially transverse to the first axis 38. For example, the second axis 42 can be perpendicular to the first axis 38. However, in further examples, the second axis 42 is not so limited to this transverse orientation, and could extend at other angles with respect to the first axis 38. Of course if the array 30 has a curvature, the second direction can follow the curvature.

Each of the columns 40 includes a plurality of the sensor elements 34. In the shown example, the columns 40 can each include eight sensor elements in a sequence, though the columns 40 could include as few as one or more sensor elements or greater than eight sensor elements. The sensor elements 34 within each of the columns 40 are generally equidistant from each other, such that the sensor elements 34 are substantially equally spaced from adjacent sensor elements along the length of the sensor array 30. In further examples, the sensor elements 34 could be spaced closer together or farther apart than as shown. By spacing the sensor elements 34 apart, signal cross talk between sensor elements 34 is limited/reduced. In the shown example, there are eight columns arranged in a non-staggered orientation (i.e., one column next to another column), though in further examples, the columns 40 could be staggered with respect to adjacent columns.

The matrix formation of the sensor array 30 includes the rows 36 and columns 40 as shown in FIG. 2. In the shown example, there are a total of eight rows and eight columns. As such, the sensor elements 34 in the matrix formation include an 8×8 matrix formation. It is to be appreciated that the matrix formation is not limited to the 8×8 matrix formation. In further examples, the matrix formation could be larger or smaller than as shown, such as by including a 9×9 matrix formation (or larger), or by including a 7×7 matrix formation (or smaller).

In further examples, the matrix formation is not limited to including an equal number of sensor elements 34 in each of the columns 40 and rows 36. Rather, the matrix formation may include columns 40 and rows 36 having different numbers of sensor elements 34. In some examples, the matrix formation includes an 8×6 matrix formation, a 6×8 matrix formation, or the like. In other examples, each of the rows and/or each of the columns could have a different number of sensor elements 34 than in adjacent rows or columns, respectively. For instance, one of the rows could have eight sensor elements while another row has a larger or smaller number of sensor elements. Likewise, one of the columns could have eight sensor elements while other columns have a larger or smaller number of sensor elements. Accordingly, the matrix formation is not limited to the example as shown in FIG. 2, and could include nearly any combination of sensor elements arranged in rows 36 and columns 40. The matrix formation is not limited to including the rectangularly shaped configuration of sensor elements 34. In yet another example, the matrix formation can include the sensor elements 34 arranged in an "X" type shape, "T" type shape, or the like.

Figure 3:
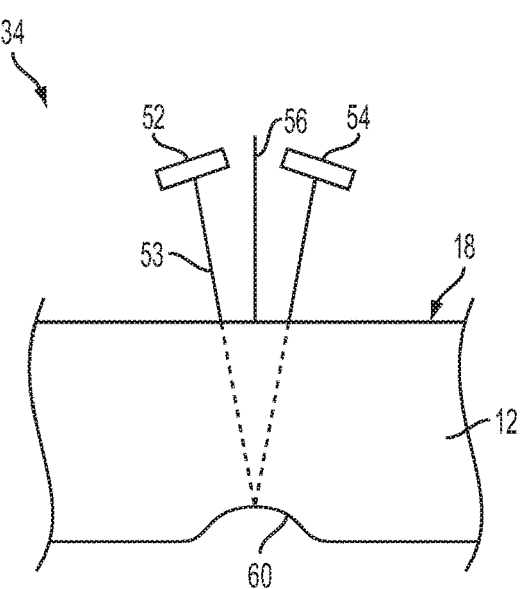
FIG. 3 is a schematic view of one example sensor element for use in the sensor array of FIG. 2.

Turning now to FIG. 3, the sensor elements 34 will be described in more detail. It is to be appreciated that while FIG. 3 depicts only one sensor element 34, the remaining, unshown sensor elements 34 may be similar or identical in shape, structure, and function as the sensor element 34 shown in FIG. 3. Moreover, the sensor element 34 is not shown in attachment with the supporting material 32 for illustrative purposes and to more clearly depict portions of the sensor element 34. However, in operation, the sensor elements 34 will be supported by (e.g., attached to) the supporting material 32.

Each sensor element 34 further includes a transmitter 52. The transmitter 52 is supported (e.g., fixed) to the supporting material 32 and spaced a distance away from the outer surface 18 of the test object 12. The transmitter 52 can transmit one or more signals 53, such as energy, pulses, and/or other impulses, into the test object 12. As is generally known, the transmitter 52 can be controlled such that the signal 53 has various timings, durations, shapes, etc. Similarly, the signal 53 includes any number of frequencies, depending on the material of the test object 12. It is to be appreciated that the signal 53 is somewhat generically depicted in FIG. 3 as a straight line. In operation, the signal 53 need not travel along a linear path, and could include bends or the like as a result of being transmitted into the test object 12.

Each sensor element 34 further includes a receiver 54 attached to the supporting material 32. The receiver 54 is supported (e.g., fixed) to the supporting material 32 and spaced a distance away from the outer surface 18 of the test object 12. The receiver 54 can receive the reflected signals 53 from the transmitter 52. In particular, the receivers 54 of each of the sensor elements 34 receive the signals 53 after the signals 53 have reflected from within the test object 12. The receiver 54 is spaced a distance away from the transmitter 52. In one example, to further improve transmission and reception of the signal 53, the receiver 54 is separated from the transmitter 52 by an acoustic barrier 56. The acoustic barrier 56 is somewhat generically depicted, as it is to be understood that the acoustic barrier 56 can comprise a number of different structures. In one example, the acoustic barrier 56 includes a cork material or the like, though any number of structures and materials are envisioned.

The signal 53 is used to detect a characteristic 60 of the test object 12. In the shown example of FIG. 3, the characteristic 60 includes corrosion in the test object 12. However, the characteristic 60 is not limited to including corrosion, and may further include imperfections (flaws, cracks, voids, inclusions, etc.), dimensions (wall thickness, length, etc.), or the like. Indeed, the characteristic 60 is somewhat generically depicted in FIG. 3 as it is to be appreciated that the characteristic 60 represents any number of items to be detected. Further, while the characteristic 60 is shown to be positioned at a wall of the test object 12 (e.g., an inner wall), the characteristic 60 could be positioned entirely within the walls of the test object 12.

In operation, the sensor elements 34 detect both the presence/absence of the characteristic 60 (e.g., corrosion, etc.), and can map the location of the characteristic 60 in the test object 12. For example, the transmitter 52 transmits the signal 53 into the test object 12. The signal 53 passes from the transmitter 52 and at least partially into the test object 12 (signal 53 represented in dashed-line form within the test object 12). The signal 53 may at least partially reflect from within the test object 12. In the shown example, the signal 53 can reflect from the characteristic 60 of the test object 12. The signal 53 may completely reflect off the characteristic 60 or, in other examples, may only partially reflect off the characteristic 60. The portion of the signal 53 that is reflected off the characteristic 60 is received with the receiver 54. Based on the reception of the signal 53 by the receiver 54, the ultrasonic sensor assembly 10 can detect the presence/absence and location of the characteristic 60 on the curved wall. In particular, information pertaining to the signal 53 received by the receiver 54 is sent to the controller 20. As is generally known, the controller 20 can analyze the signal 53 to determine the presence/absence and location of the characteristic 60.

Figure 4:
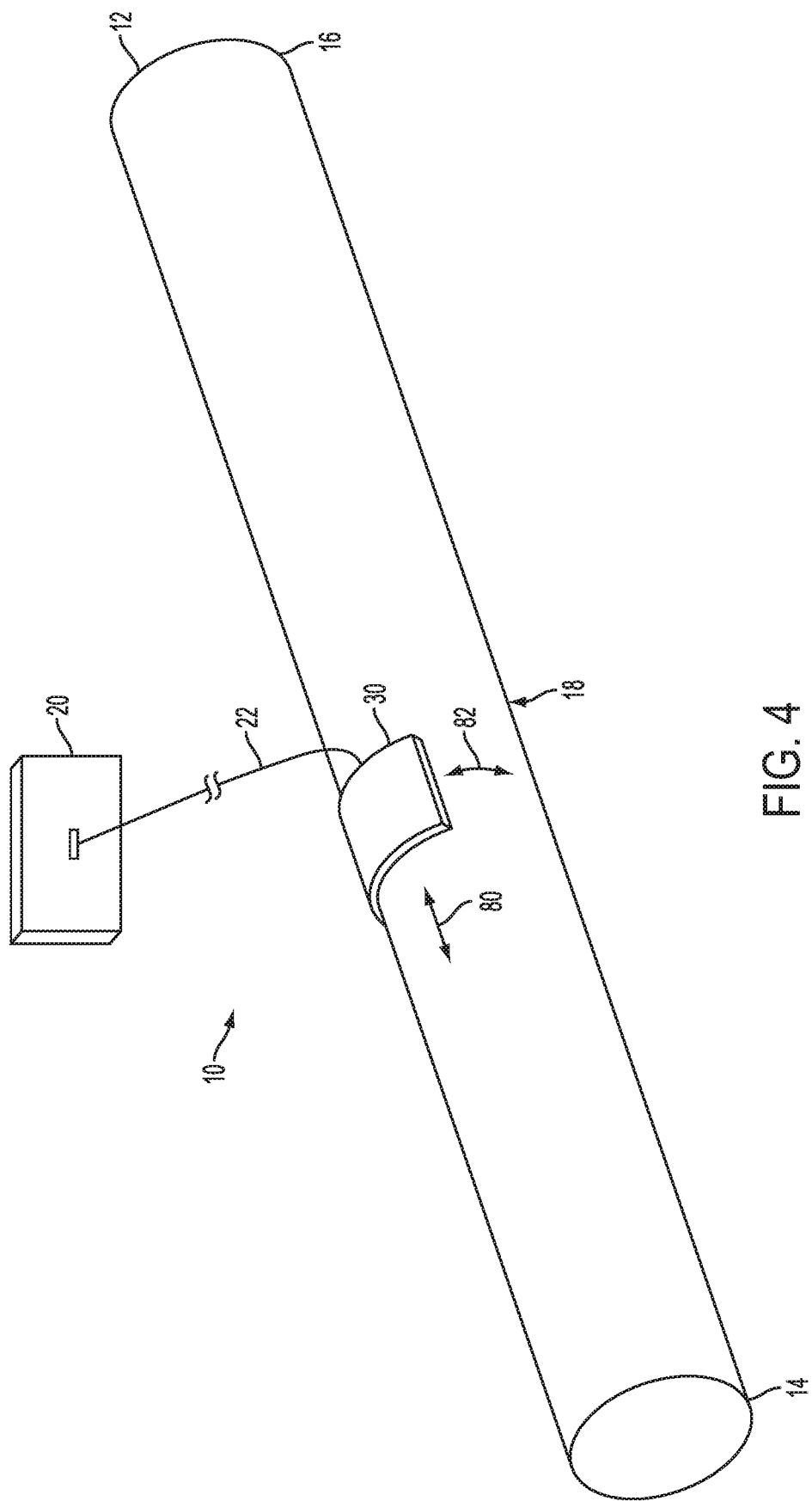
FIG. 4 is a schematic, perspective view of the example sensor array being moved with respect to the test object.

Turning now to FIG. 4, the ultrasonic sensor assembly 10 is shown in the process of mapping the characteristics 60 (e.g., corrosion) of the test object 12. In particular, the sensor array 30 is positioned in proximity to the outer surface 18 of the test object 12. The sensor array 30 is then moved with respect to the test object 12. The sensor array 30 can be moved in a variety of directions. For example, the sensor array 30 can be moved in a first direction 80 that extends along a length of the test object 12. Similarly, the sensor array 30 could be moved in a second direction 82 that is substantially transverse to the length of the test object 12. In further examples, the sensor array 30 is not limited to being moved in the first direction 80 or the second direction 82, and instead could be moved at an angle (e.g., 45° angle, etc.) with respect to the first direction 80 and second direction 82.

As the sensor array 30 is moved along the test object 12, the transmitters 52 of each of the sensor elements 34 in the sensor array 30 are triggered to transmit the signals 53. In one example, the transmitters 52 of all of the sensor elements 34 are triggered to transmit the signals 53 simultaneously. In another example, the transmitters 52 of the sensor elements 34 are not triggered simultaneously, and instead, may be triggered separately, such as by triggering only a portion of the transmitters 52 followed by another portion of the transmitters 52 to transmit the signals 53. Indeed, it is to be appreciated that the transmitters 52 of the sensor elements 34 can be triggered to transmit the signals 53 in any number of combinations (e.g., simultaneously or non-simultaneously). The receivers 54 of each of the sensor elements 34 will receive the respective signal sent from that transmitter 52 of the same sensor element 34.

The sensor elements 34 can be used to detect and map the location of the characteristics 60 in the test object 12. For example, the controller 20 may include an electronic representation of the test object 12, such as a two-dimensional or three-dimensional representation of the test object 12. As is generally known, the controller 20, in operative association with the sensor array 30, can correlate the location of the sensor array 30 respective to the test object 12 with the electronic representation of the test object 12. The controller 20 tracks the sensor array 30 as the sensor array 30 moves along the outer surface 18 of the test object 12, such as in the first direction 80 and/or second direction (or other directions). The sensor array 30 can detect the characteristics 60 of the test object 12 as the sensor array 30 is moved along the test object 12 and convey this information to the controller 20. These characteristics 60 are then mapped and stored by the controller 20 with respect to the electronic representation of the test object 12. Accordingly, the controller 20 can map and plot the characteristics 60 of the test object 12 (as detected by the sensor array 30) on the electronic representation as the sensor array 30 is moved along the test object 12.

By providing the ultrasonic sensor assembly 10 with the sensor array 30, the test object 12 can be more quickly and accurately analyzed. In particular, the sensor array 30 will detect the characteristics 60 of the test object 12 and map these characteristics on the electronic representation of the test object 12. The sensor array 30 has a larger area, thus allowing for a larger detection range of the test object 12 at one location. Further, providing the plurality of sensor elements 34 in the sensor array 30 gives more accurate detection and mapping of the characteristics 60.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An ultrasonic sensor assembly, comprising:
a controller; and
a sensor array in operative association with the controller and configured to conform to a cylindrical shape of a tubular test object, the sensor array including a flexible supporting material comprising an engineering plastic, and a plurality of operable sensor elements arranged in a matrix formation within the flexible supporting material, the matrix formation including a plurality of rows of the sensor elements and a plurality of columns of the sensor elements;
wherein the sensor array, when applied to the test object, is configured to conform to the cylindrical shape of the test object such that columns of the one or more sensor elements are oriented parallel to a longitudinal axis of the test object and rows of the one or more sensor elements are oriented transverse to the longitudinal axis of the test object.

2. The ultrasonic sensor assembly of claim 1, wherein the supporting material includes a resilient member having a predetermined curvature matching a curvature of the cylinder shape of the outer surface of the test object.

3. The ultrasonic sensor assembly of claim 1, wherein the engineering plastic comprises a polyimide material.

4. The ultrasonic sensor assembly of claim 1, wherein the ultrasonic sensor assembly includes a plurality of sensor arrays.

5. The ultrasonic sensor assembly of claim 1, wherein the sensor array is operatively associated with the controller via a wireless connection.

6. The ultrasonic sensor assembly of claim 1, wherein each sensor element includes a transmitter and a receiver.

7. The ultrasonic sensor assembly of claim 6, wherein each sensor element includes an acoustic barrier separating the transmitter and the receiver.

8. The ultrasonic sensor assembly of claim 7, wherein the acoustic barrier comprises a cork material.

9. The ultrasonic sensor assembly of claim 6, wherein the test object has an outer surface and, for each sensor element, the flexible supporting material and the transmitter are configured such that the transmitter is supported by the flexible supporting material at a spaced distance away from the outer surface of the test object.

10. The ultrasonic sensor assembly of claim 6, wherein the test object has an outer surface and, for each sensor element, the flexible supporting material and the receiver are configured such that the receiver is supported by the flexible supporting material at a spaced distance away from the outer surface of the test object.

11. The ultrasonic sensor assembly of claim 1, wherein the sensor elements are configured to detect a characteristic in the test object and transmit the detected characteristic to the controller.

12. The ultrasonic sensor assembly of claim 11, wherein the controller is configured to map a location of the detected characteristic with respect to a corresponding location included in an electronic representation of the test object.

13. The ultrasonic sensor assembly of claim 12, wherein the electronic representation includes a multi-dimensional representation of the test object.

14. The ultrasonic sensor assembly of claim 13, wherein the controller includes one or more programs configured to provide the electronic representation in a user interface via a display.

15. A method for testing a tubular test object using an ultrasonic sensor assembly, the method comprising:
attaching an ultrasonic sensor array of an ultrasonic sensor assembly to a cylindrical test object such that a flexible supporting material comprising an engineering plastic conforms to a curvature of the cylindrical shape of the test object; and operating the ultrasonic sensor assembly to cause a transmitter on each of a plurality of sensor elements embedded within the flexible supporting material as a matrix formation to emit a signal into the test object, and to cause a receiver on each of the plurality of sensor elements to detect a reflected signal from the test object, the receiver being acoustically isolated from the transmitter by an acoustic barrier; and providing the reflected signal to a controller in operative association with the ultrasonic sensor array to determine a characteristic of the test object based on the reflected signal.

16. The method of claim 15, wherein attaching the sensor array includes orienting columns of the one or more sensor elements parallel to a longitudinal axis of the test object and orienting rows of the one or more sensor elements transverse to the longitudinal axis of the test object.

17. The method of claim 15, wherein the sensor elements detect a dimension at one or more locations of the test object based on the reflected signal and transmit the detected dimension to the controller.

18. The method of claim 17, wherein the controller maps a location of the detected dimension with respect to a corresponding location included in an electronic representation of the test object.

19. The ultrasonic sensor assembly of claim 18, wherein the electronic representation includes a multi-dimensional representation of the test object.

20. The ultrasonic sensor assembly of claim 18, wherein the controller includes one or more programs that provide the electronic representation in a user interface via a display.

\* \* \* \* \*